United States Patent [19]

Thomas, Jr.

[11] 4,103,033
[45] Jul. 25, 1978

[54] METHOD OF CONTROLLING INSECTS

[75] Inventor: Victor M. Thomas, Jr., San Jose, Calif.

[73] Assignee: Stauffer Chemical Company, Westport, Conn.

[21] Appl. No.: 760,785

[22] Filed: Jan. 19, 1977

[51] Int. Cl.² ............................................. A01N 9/24
[52] U.S. Cl. ........................... 424/343; 424/DIG. 12
[58] Field of Search ....................... 424/343, DIG. 12

[56] References Cited
PUBLICATIONS

Annual Review of Biochemistry, vol. 40, pp. 1096–1097, (1971).
Chemical Abstracts 82:73214a (1975).
Chemical Abstracts 83:40179k (1975).

*Primary Examiner*—Leonard Schenkman
*Attorney, Agent, or Firm*—Edwin H. Baker

[57] ABSTRACT

The compound 2-bromo-8-chloro-1,1,9-trimethyl-4-methylene-spiro[5.5] undec-8-en-3-ol is used to effectively control insects.

1 Claim, No Drawings

METHOD OF CONTROLLING INSECTS

This invention relates to a method of controlling insects with the compound 2-bromo-8-chloro-1,1,9-trimethyl-4-methylene-spiro[5.5]undec-8-en-3-ol.

The compound 2-bromo-8-chloro-1,1,9-trimethyl-4-methylene-spiro[5.5]undec-8-en-3-ol is a sesquiterpene chamigrene compound of the formula

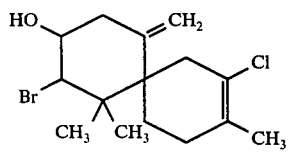

This chamigrene compound has been reported to have been isolated from *Laurencia elata* by J. J. Sims, G. H. Y. Lin and R. M. Wing who refer to it as elatol in *Tetrahedron Letters* No. 39, pp 3487–3490 (1974), Pergamon Press. The same compound has also been found to exist in *Laurencia pacifica* as reported by W. Fenical and J. N. Norris in *Journal of Phycology* Volume 11, pp 104–108 (1975). The compound is also referred to in a review article *Halogenation in the Rhodophyta: A Review* by W. Fenical which appears in *Journal of Phycology* Volume 11, pp 245–259 (1975).

It has now been discovered that the compound 2-bromo-8-chloro-1,1,9-trimethyl-4-methylene-spiro[5.5]undec-8-en-3-ol possesses unusual insecticidal activity. Accordingly, this invention comprises a method for the control of insects by applying to the locus where control is desired an insecticidally effective amount of the compound 2-bromo-8-chloro-1,1,9-trimethyl-4-methylene-spiro[5.5]undec-8-en-3-ol.

The following evaluations demonstrate the insecticidal effectiveness of this compound.

Anti-Juvenile Hormone Assay

Milkweed Bug (*Oncopeltus fasciatus*)

The compound is diluted in acetone and impregnated onto a 9.0-cm filter paper disc by applying 0.5 ml and letting it completely evaporate. Ten 2nd-instar nymphs of *Oncopeltus fasciatus* are placed in a 9.0-cm petri dish with the treated filter paper. The nymphs are supplied with milkweed seeds and water (soaked dental cotton in a 4-dram vial cap). All petri dishes are stored at 70° F for the entire life cycle of the insect (about one month). In testing 2-bromo-8-chloro-1,1,9-trimethyl-4-methylene-spiro[5.5]undec-8-en-3-ol, 50% mortality resulted at a testing concentration of about 0.4 μg/ml.

Ovicide Assay

Cabbage Looper (*Trichloplusia ni*)

Masses of newly laid eggs of the cabbage looper are dipped in acetone solutions of the test chemicals and placed in petri dishes containing a portion of larval rearing medium. Treated eggs are maintained at 78° F and mortality is recorded after all control eggs have hatched and the young larvae are feeding on the media. Test concentrations range from 1% down to that at which approximately 50% of the treated eggs hatch, which for 2-bromo-8-chloro-1,1,9-trimethyl-4-methylene-spiro[5.5]undec-8-en-3-ol was 0.8%.

The insecticidal compound appears to have a highly unusual mode of action and is believed to interfere with the metamorphosis of the insect. Thus, the compound is preferably applied to the insects at a pre-adult stage of the life cycle. The compound is generally applied to the locus where control of insects is desired in the form of formulations containing the compound and an inert carrier. Insecticidal formulations generally take the form of dusts, wettable powders, solutions, emulsifiable concentrates or the like.

Dusts are free-flowing powder compositions containing the insecticidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired. The composition generally contains up to 50% of active ingredient.

Wettable powders are finely divided compositions comprising a particulate carrier impregnated with the insecticidal compound and additionally containing one or more surface active agents. The surface active agents promote rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in *Pesticide Formulations* by Wade Van Valkenburg, Marcel Dekker, Inc., N.Y. 1973 at pages 79–84.

Granules comprise the insecticidal compound impregnated on a particulate inert carrier having a particle size of 1 to 2 millimeters in diameter. The granules can be mady by spraying a solution of the active ingredient in a volatile solvent onto the granular carrier. Suitable carriers in preparation of granules include clay, vermiculite, sawdust, granular carbon, and the like.

The insecticidal compounds can also be applied to the soil in the form of a solution in a suitable solvent. Solvents frequently used in pesticidal formulations include kerosene, fuel oil, xylene, petroleum fractions with boiling ranges above xylene, and aromatic petroleum fractions rich in methylated naphthalenes.

Emulsifiable concentrates consist of an oil solution of the insecticidal compound along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

The compositions are applied to the locus where control of insects is desired in an insecticidally effective amount. This amount will vary greatly, depending on the particular insect to be controlled. The amount required in a particular situation can be readily ascertained by one skilled in the art. In a preferred method of application, the insecticidal compound is applied as a solution or suspension from conventional spray apparatus. The solutions or suspensions contain about 0.01 to about 5.0%, preferably about 0.1 to about 2.0% by weight of the compound.

What is claimed is:

1. A method for controlling the growth of insects selected from *Oncopeltus fasciatus* or *Trichloplusia ni* at a pre-adult stage of the life cycle which comprises applying to the locus where such control is desired, an insecticidally effective amount of 2-bromo-8-chloro-1,1,9-trimethyl-4-methylene-spiro[5.5]undec-8-en-3-ol.

* * * * *